United States Patent
Chen et al.

(10) Patent No.: US 11,399,896 B2
(45) Date of Patent: Aug. 2, 2022

(54) SURGICAL TOOL TIP AND ORIENTATION DETERMINATION

(71) Applicant: Sony Corporation, Tokyo (JP)

(72) Inventors: Xiaojing Chen, Santa Clara, CA (US); Ko-Kai Albert Huang, Cupertino, CA (US); Ming-Chang Liu, San Jose, CA (US)

(73) Assignee: Sony Group Corporation, Tokyo (JP)

( * ) Notice: Subject to any disclaimer, the term of this patent is extended or adjusted under 35 U.S.C. 154(b) by 46 days.

(21) Appl. No.: 16/447,514

(22) Filed: Jun. 20, 2019

(65) Prior Publication Data
US 2020/0397509 A1 Dec. 24, 2020

(51) Int. Cl.
*G06K 9/00* (2022.01)
*A61B 34/20* (2016.01)
*A61B 90/00* (2016.01)
*A61B 34/30* (2016.01)

(52) U.S. Cl.
CPC .............. *A61B 34/20* (2016.02); *A61B 90/36* (2016.02); *A61B 34/30* (2016.02); *A61B 2034/2055* (2016.02); *A61B 2090/0811* (2016.02)

(58) Field of Classification Search
CPC . A61B 34/20; A61B 90/36; A61B 2034/2055; A61B 34/30; A61B 2090/0811
USPC ....................................................... 382/128
See application file for complete search history.

(56) References Cited

U.S. PATENT DOCUMENTS

| | | | |
|---|---|---|---|
| 9,867,669 B2 | 1/2018 | Zhao et al. | |
| 10,675,098 B2* | 6/2020 | Zhao | A61B 34/37 |
| 2014/0241577 A1 | 8/2014 | Kwak | |
| 2015/0297313 A1 | 10/2015 | Reiter | |
| 2018/0078315 A1 | 3/2018 | Ren | |
| 2018/0122070 A1 | 5/2018 | Chou | |
| 2018/0158209 A1 | 6/2018 | Fine | |
| 2019/0380789 A1* | 12/2019 | Link | A61B 34/25 |

OTHER PUBLICATIONS

Yakui Chu, Xilin Yang, Yuan Ding, Danni Ai, Jingfan Fan, Xu Li, Yongtian Wang, Jian Yang, "FSNet: Pose Estimation of Endoscopic Surgical Tools Using Feature Stacked Network," Proceedings of 2019 the 9th International Workshop on Computer Science and Engineering, pp. 427-431, Jun. 15-17, 2019 (Year: 2019).*

Du, Xiaofei, et al. "Articulated multi-instrument 2-D pose estimation using fully convolutional networks." IEEE transactions on medical imaging 37.5 (2018): 1276-1287. (Year: 2018).*

(Continued)

*Primary Examiner* — Jonathan S Lee
(74) *Attorney, Agent, or Firm* — Trellis IP Law Group, PC

(57) ABSTRACT

Implementations generally relate to determining the position of a tool tip of a surgical instrument and the orientation of the surgical instrument. In some implementations, a method includes receiving at least one image frame of a plurality of image frames. The method further includes detecting a surgical tool in the at least one image frame. The method further includes determining a position of a tip of the surgical tool. The method further includes determining an orientation of the surgical tool.

20 Claims, 8 Drawing Sheets

(56) References Cited

OTHER PUBLICATIONS

Kurmann, Thomas, et al. "Simultaneous recognition and pose estimation of instruments in minimally invasive surgery." International Conference on Medical Image Computing and Computer-Assisted Intervention. Springer, Cham, 2017. (Year: 2017).*

Rieke, Nicola, et al. "Real-time localization of articulated surgical instruments in retinal microsurgery." Medical image analysis 34 (2016): 82-100. (Year: 2016).*

Van der Stap, N., et al. "The use of the focus of expansion for automated steering of flexible endoscopes." 2012 4th IEEE RAS & EMBS International Conference on Biomedical Robotics and Biomechatronics (BioRob). IEEE, 2012. (Year: 2012).*

Zhao, Zijian, et al. "Real-time surgical instrument detection in robot-assisted surgery using a convolutional neural network cascade." Healthcare technology letters 6.6 (2019): 275. (Year: 2019).*

Sarikaya, Duygu, Jason J. Corso, and Khurshid A. Guru. "Detection and localization of robotic tools in robot-assisted surgery videos using deep neural networks for region proposal and detection." IEEE transactions on medical imaging 36.7 (2017): 1542-1549. (Year: 2017).*

Bodenstedt, Sebastian, et al. "Comparative evaluation of instrument segmentation and tracking methods in minimally invasive surgery." arXiv preprint arXiv:1805.02475 (2018). (Year: 2018).*

Austin Reiter, et al.; Appearance learning for 3D tracking of robotic surgical tools; The International Journal of Robotics Research published online Nov. 11, 2013: http://web2.cs.columbia.edu/~allen/PAPERS/austin_ijrr.pdf.

David Bouget, et al; Detecting Surgical Tools by Modelling Local Appearance and Global Shape; IEEE Transactions on Medical Imaging, vol. 34, No. 12, Dec. 2015 https://rodrigob.github.io/documents/2015_tmi_bouget_et_al_detecting_surgical_tools.pdf.

Al Hajj Hassan et al: "Surgical tool detection in cataract surgery videos through multi-image fusion inside a convolutional neural network".

Sarikaya Duygu te al: "Detection and Localization of Robotic Tools in Robot-Assisted Surgery Videos Using Deep Neural Networks for Region Proposal and Detection".

Wesierski Daniel et al: "Instrument detection and pose estimation with rigid part mixtures model in video-assisted surgeries", Medical Image Analysis, Oxford University Press, Oxofrd, GB.

* cited by examiner

SURGICAL TOOL TIP AND ORIENTATION DETERMINATION

BACKGROUND

Computer-assisted surgery uses computer technology for guiding or performing medical procedures such as procedures involving endoscopy, laparoscopy, etc. During surgery, a surgeon may need to use various tools to perform surgery. A camera and monitor can help a surgeon to manipulate multiple surgical tools using robotic arms. However, it can be difficult to view surgical tools well on a monitor during surgery.

SUMMARY

Implementations generally relate determining the position of a tool tip of a surgical instrument and the orientation of the surgical instrument. In some implementations, a system includes one or more processors, and includes logic encoded in one or more non-transitory computer-readable storage media for execution by the one or more processors. When executed, the logic is operable to cause the one or more processors to perform operations including receiving at least one image frame of a plurality of image frames; detecting a surgical tool in the at least one image frame; determining a position of a tip of the surgical tool; and determining an orientation of the surgical tool.

With further regard to the system, in some implementations, the logic when executed is further operable to perform operations comprising generating a plurality of key points of the surgical tool, and wherein each key point of the plurality of key points corresponds to a different portion of the surgical tool. In some implementations, the logic when executed is further operable to perform operations comprising determining a plurality of key points of the surgical tool, wherein at least one key point of the plurality of key points corresponds to the tip of the surgical tool; and determining the position of the tip of the surgical tool based on the at least one key point that corresponds to the tip of the surgical tool. In some implementations, the logic when executed is further operable to perform operations comprising generating a plurality of key points of the surgical tool; and determining the orientation of the surgical tool based on the plurality of key points. In some implementations, the logic when executed is further operable to perform operations comprising determining the position of the tip of the surgical tool and determining the orientation of the surgical tool in real-time. In some implementations, the logic when executed is further operable to perform operations comprising: generating a plurality of key points of the surgical tool; and determining a key point confidence score for each key point of the surgical tool. In some implementations, the logic when executed is further operable to perform operations comprising determining the position of the tip of the surgical tool and determining the orientation of the surgical tool based on deep learning.

In some embodiments, a non-transitory computer-readable storage medium with program instructions thereon is provided. When executed by one or more processors, the instructions are operable to cause the one or more processors to perform operations including receiving at least one image frame of a plurality of image frames; detecting a surgical tool in the at least one image frame; determining a position of a tip of the surgical tool; and determining an orientation of the surgical tool.

With further regard to the computer-readable storage medium, in some implementations, the instructions when executed are further operable to perform operations comprising generating a plurality of key points of the surgical tool, and wherein each key point of the plurality of key points corresponds to a different portion of the surgical tool. In some implementations, the instructions when executed are further operable to perform operations comprising generating a plurality of key points of the surgical tool, wherein at least one key point of the plurality of key points corresponds to the tip of the surgical tool; and determining the position of the tip of the surgical tool based on the at least one key point that corresponds to the tip of the surgical tool. In some implementations, the instructions when executed are further operable to perform operations comprising generating a plurality of key points of the surgical tool; and determining the orientation of the surgical tool based on the plurality of key points. In some implementations, the instructions when executed are further operable to perform operations comprising determining the position of the tip of the surgical tool and determining the orientation of the surgical tool in real-time. In some implementations, the instructions when executed are further operable to perform operations comprising generating a plurality of key points of the surgical tool; and determining a key point confidence score for each key point of the surgical tool. In some implementations, the instructions when executed are further operable to perform operations comprising determining the position of the tip of the surgical tool and determining the orientation of the surgical tool based on deep learning.

In some implementations, a method includes receiving at least one image frame of a plurality of image frames. The method further includes detecting a surgical tool in the at least one image frame. The method further includes determining a position of a tip of the surgical tool. The method further includes determining an orientation of the surgical tool.

With further regard to the method, in some implementations, the method further includes generating a plurality of key points of the surgical tool, and wherein each key point of the plurality of key points corresponds to a different portion of the surgical tool. In some implementations, the method further includes determining a plurality of key points of the surgical tool, wherein at least one key point of the plurality of key points corresponds to the tip of the surgical tool; and determining the position of the tip of the surgical tool based on the at least one key point that corresponds to the tip of the surgical tool. In some implementations, the method further includes generating a plurality of key points of the surgical tool; and determining the orientation of the surgical tool based on the plurality of key points. In some implementations, the method further includes determining the position of the tip of the surgical tool and determining the orientation of the surgical tool in real-time. In some implementations, the method further includes generating a plurality of key points of the surgical tool; and determining a key point confidence score for each key point of the surgical tool.

A further understanding of the nature and the advantages of particular implementations disclosed herein may be realized by reference of the remaining portions of the specification and the attached drawings.

DETAILED DESCRIPTION

Implementations generally relate to determining the position of a tool tip of a surgical instrument and the orientation of the surgical instrument. As described in more detail herein, a system receives an image frame from a camera. In various implementations, the image frame may be one of a series of image frames of a video stream. The system detects a surgical instrument or tool in the at least one of the image frames. The system further determines the position of the tip of the surgical tool. The system also determines the orientation of the surgical tool.

Figure 1:
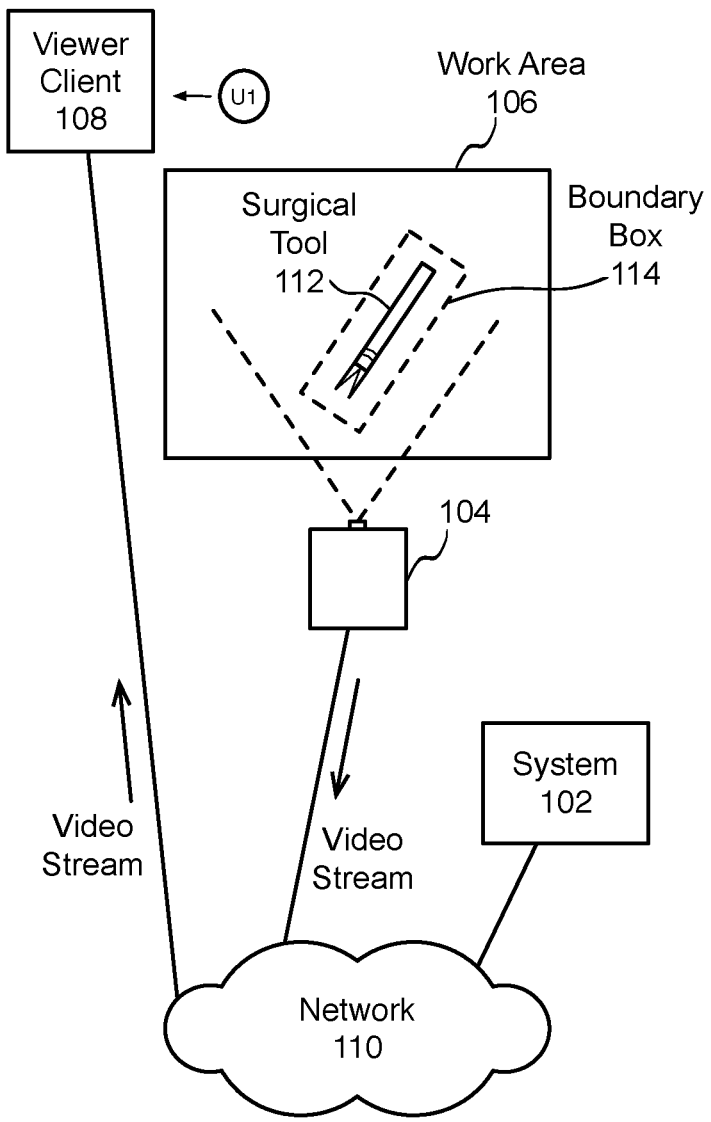
FIG. 1 illustrates a block diagram of an example work environment, which may be used for implementations described herein.

FIG. 1 illustrates a block diagram of an example work environment 100 which may be used for implementations described herein. Shown is a system 102, which performs various implementations described herein. System 102 controls a camera 104, which captures video of a work area 106, or surgery area. The video may be a surgical video recorded by camera 104. System 102 causes camera 104 to send the video stream from camera 104 to viewer client 108 via a network 110. In various implementations, the video may be used to facilitate a user such as a surgeon during laparoscopic surgery. For example, as the surgeon handles a surgical tool 112 shown in work area 106 to interact with tissues, the surgeon may watch a visual image of the surgical tool 112 interacting with the tissues. In various implementations, the surgeon may also watch a visual image of the surgical tool 112 whether the surgeon is handling surgical tool 112 directly with the surgeon's hand and/or with a robotic arm. As described in more detail herein, system 102 analyzes the characteristics of surgical tool 112, which is captured by camera 104.

Figure 2:
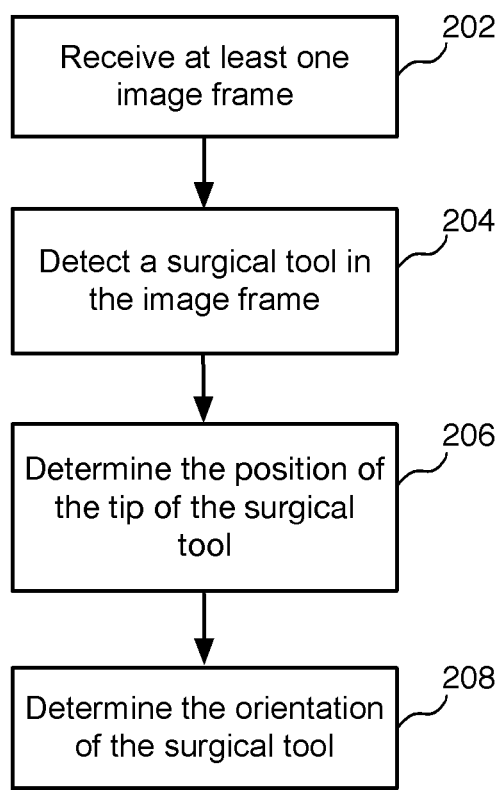
FIG. 2 illustrates an example flow diagram for determining the position of a tool tip of a surgical instrument and the orientation of the surgical instrument, according to some implementations.

FIG. 2 illustrates an example flow diagram for determining the position of a tool tip of a surgical instrument and the orientation of the surgical instrument, according to some implementations. As described in more detail below, the system performs various functions including determining the position of the tool tip of a surgical instrument. Referring to both FIGS. 1 and 2, a method is initiated at block 202, where the system such as system 102 receives at least one image frame. In various implementations, the received image frame is from a sequence of image frames that the system accesses or obtains from a video stream. The video stream may be a surgical video, for the example.

At block 204, system 102 detects a surgical tool such as surgical tool 112 in the image frame. In some implementations, the system first detects one or more objects in the received image frame. System 102 may use object recognition techniques to detect specific objects in the received image.

Figure 3:
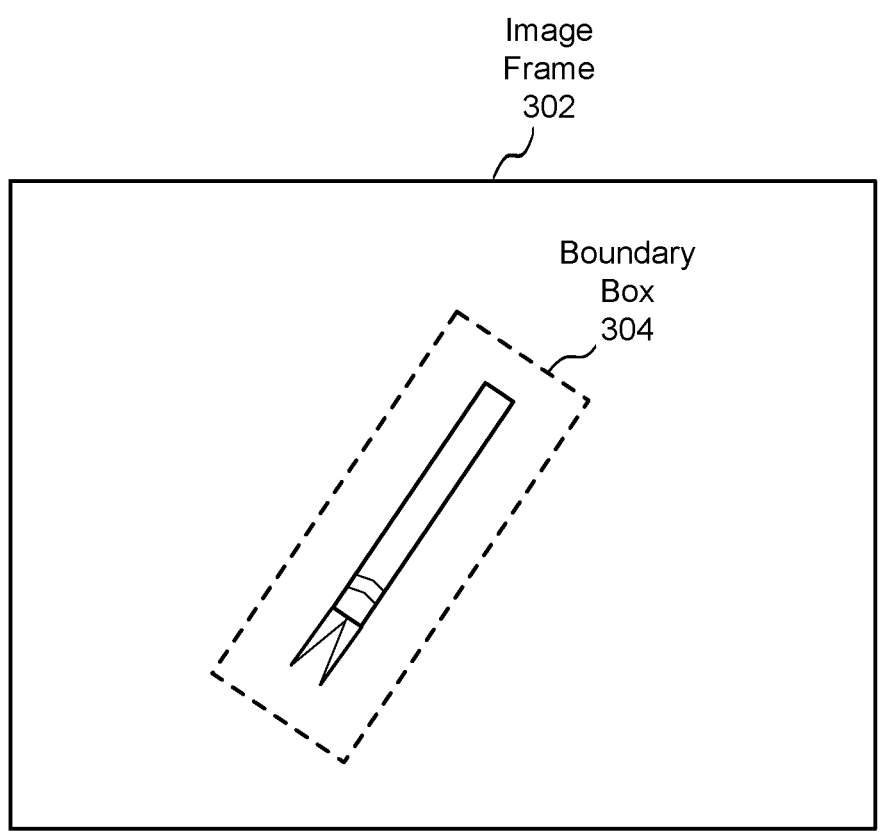
FIG. 3 illustrates an example image frame including a surgical tool and a boundary box, according to some implementations.

FIG. 3 illustrates an example image frame 302 including surgical tool 112 and a boundary box 304, according to some implementations. As shown, in various implementations, the system initially detects surgical tool 112 or targeted image in the scene shown in image frame 302 within boundary box 304.

Boundary box 304 is a visual indicator that demarcates surgical tool 112. While boundary box 304 is shown as a rectangle, the actual shape and size of boundary box 304 may vary depending on the shape and size of the surgical tool.

At block 206, system 102 determines the position of the tip of the surgical tool. In various implementations, the system determines the position of the tip of the surgical tool based on key points that the system generates.

Figure 4:
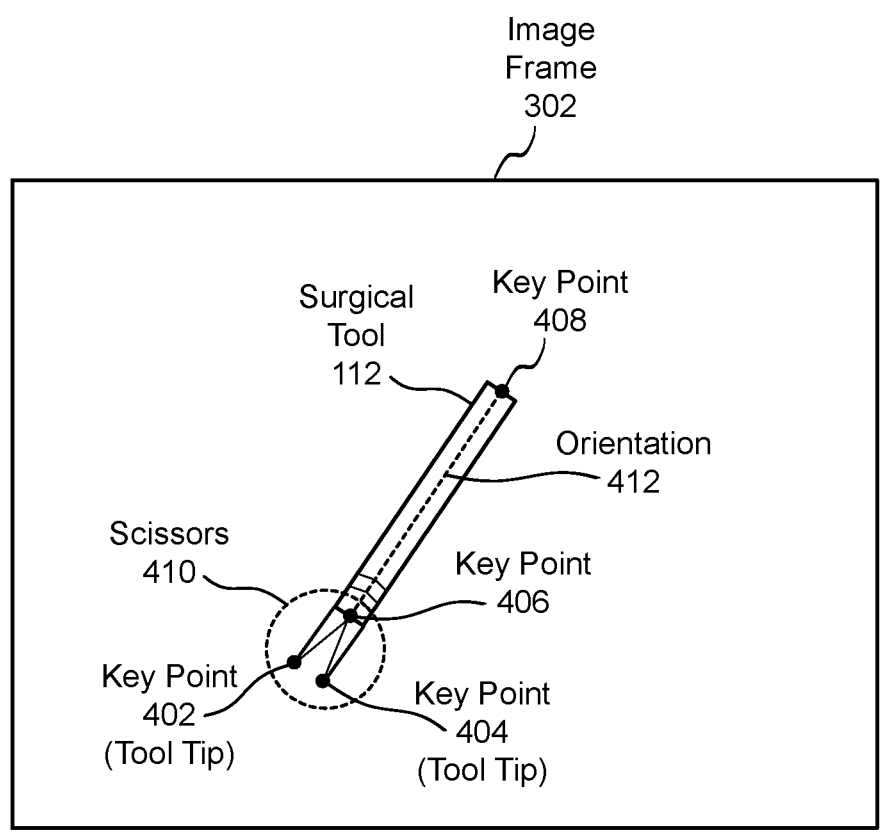
FIG. 4 illustrates an example image frame including a surgical tool and key points, according to some implementations.

FIG. 4 illustrates example image frame 302 including surgical tool 112 and key points, according to some implementations. Shown are key points 402, 404, 406, and 408 at various locations on surgical tool 112. Key points 402 are 404 positioned or located at the tips of surgical tool 112. In this particular example, surgical tool 112 includes scissors 410, and key points 402 and 404 are located at the tips of scissors 410.

While four key points are shown, the particular number of key points may vary depending on the number of components, configuration, and shape of the surgical tool. Also, the particular number and positions of the key points may vary depending on the number of components, configuration, and shape of the surgical tool. Example implementations directed to determining the position of the tip of the surgical tool are described in more detail below in connection with FIG. 5.

At block 208, system 102 determines the orientation of surgical tool 112. In various implementations, the system determines the position of the surgical tool tip based on key points that the system generates. Referring still to FIG. 4, key points 406 and 408 define the orientation 412 of surgical tool 112. Example implementations directed to determining the orientation of the surgical tool tip are described in more detail below in connection with FIG. 6.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

Surgical tool tip position and orientation are important information for surgeons and may be used in many applications. For example, the surgical tool tip and orientation may provide visual feedback to a surgeon for safety purposes. In some implementations, knowing the position of the surgical tool tip, the system may zoom in on the relevant work area so that the surgeon better views the interaction between the surgical tool and target tissues. In other words, implementations provide the surgeon with an optimal viewing angle. This minimizes or eliminates the surgical tool tip from being blocked by other objects such as non-target tissues, other tools such as assistive tools in the work or surgery area. In some implementations, the system may locally enhance the quality of the image around the surgical tool tip of tool as the system tracks the movement of the surgical tool tip.

Implementations also facilitate in the assessment of performance of a surgeon during training. For example, the information may be used to determine the accuracy and/or efficiency of the surgeon during a surgery. Such information may be used to compare the performance of a surgeon in training to the performance of an experienced surgeon. Furthermore, localization of the surgical tool tip enables proximity estimation to surgical targets (e.g., eye retina, etc.) by aligning a cross-sectional view in an application such as optical coherence tomography (OCT), for example. Other example application areas may include natural user interface design, automatic warning systems, semantic feedback systems, skill assessment systems, etc.

Figure 5:
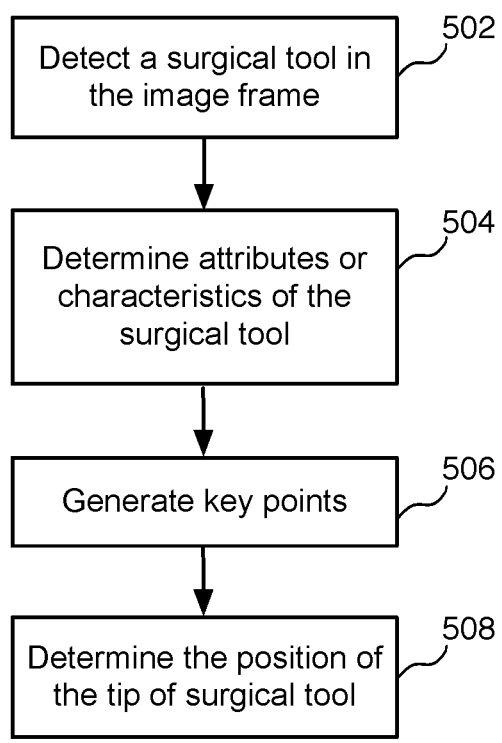
FIG. 5 illustrates an example flow diagram for determining the position of a tool tip of a surgical instrument and the orientation of the surgical instrument, according to some implementations.

FIG. 5 illustrates an example flow diagram for determining the position of a tool tip of a surgical instrument and the orientation of the surgical instrument, according to some implementations. Referring to both FIGS. 4 and 5, a method is initiated at block 502, where the system such as system 102 detects an object such as surgical tool 112 in image frame 302. In some implementations, the system first detects one or more objects in the received image frame. System 102 may use object recognition techniques to detect objects in image frame 302.

At block 504, the system determines attributes or characteristics of surgical tool 112. For example, attributes of surgical tool 112 may include components of surgical tool 112, the configuration of surgical tool 112 and its components, the shape of surgical tool 112, etc. The particular attributes of surgical tool 112 that the system determines may vary, depending on the surgical tool or targeted object detected and identified in the image frame.

At block 506, the system generates key points 402, 404, 406, and 408 of the surgical tool. In various implementations, the system generates the key points based on the attributes of surgical tool 112. In various implementations, each key point corresponds to a different portion of the surgical tool. For example, as shown in FIG. 4, key points 402, 404, 406, and 408 correspond to points or locations of surgical tool 112. In some implementations, the system matches key points 402 to 408 to pre-defined key points of a known type of surgical tool, where the number of key points and relative locations of the key points correspond to pre-defined points or locations of the known surgical tool.

At block 508, the system determines the position of the tip of surgical tool 112 based on key points 402, 404, 406, and 408. For example, at least one of the key points corresponds to the tip of the surgical tool. System 102 determines the position of the tip of the surgical tool based on the one key point that corresponds to the tip of the surgical tool.

The number of tool tips may vary, depending on the particular implementation. For example, in the implementation shown, surgical tool 112 includes a scissors 410. The system may identify scissors 410 based on the shape of that portion of surgical tool 112. The system may also determine that key point 402 is a tool tip and that key point 404 is a tool tip.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

Figure 6:
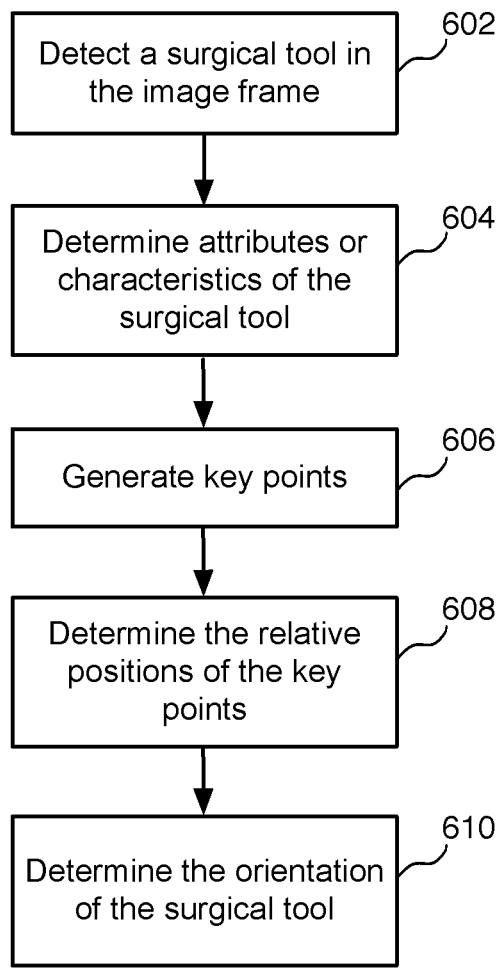
FIG. 6 illustrates an example flow diagram for determining the position of a tool tip of a surgical instrument, according to some implementations.

FIG. 6 illustrates an example flow diagram for determining the position of a tool tip of a surgical instrument, according to some implementations. Referring to both FIGS. 4 and 6, a method is initiated at block 602, where the system such as system 102 detects an object such as surgical tool 112 in image frame 302. In some implementations, the system first detects one or more objects in the received image frame. System 102 may use object recognition techniques to detect objects in image frame 302.

At block 604, the system determines attributes or characteristics of surgical tool 112. The system may determine such attributes or characteristics in a manner similar to implementations described in connection with block 504 of FIG. 5.

At block 606, the system generates key points 402, 404, 406, and 408 based on the attributes of surgical tool 112. The system may determine such attributes or characteristics in a manner similar to implementations described in connection with block 506 of FIG. 5. In various implementations, the key points may function as landmarks that map portions of the surgical tool.

At block 608, the system determines the relative positions of key points 402, 404, 406, and 408. For example, the system may determine the distance between different key point pairs.

At block 610, the system determines the orientation of surgical tool 112. In various implementations, the system determines the orientation of the surgical tool based on the plurality of key points. The system may determine linear lines between key points (e.g., key point 406 and key point 406), and determine that the portion of the surgical tool between the two key points is a handle or shaft. For example, the system may determine that the key point 406 as at the distal end of the shaft of surgical tool 112 and that key point 408 as at the proximal end of the shaft of surgical tool 112.

For ease of illustration, the orientation of surgical tool 112 is indicated generally by the orientation of the shaft. In various implementations, the system also determines the orientation of multiple portions of surgical tool 112. For example, the system may determine the orientation of each blade of scissors 410 as scissors 410 opens and closes, and as surgical tool 112 moves in general.

The system may also determine the series or line of key points in order to determine the length of the surgical tool and/or length of portions of the surgical tool. If the surgical tool has multiple portions such as a main body and a specialty portion (e.g., scissors, grabber, etc.), the system may also determine the angle or angles between two or more portions of the surgical tool.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

In various implementations, the location or position of the surgical tool tip and the orientation of the surgical tool are two-dimensional (2D) relative to image frame and other objects (e.g., tissue, assistive or secondary tools, etc.). This helps the surgeon to handle surgical tool 112 and to minimize or eliminate the tip of surgical tool 112 from being blocked by other objects. In some implementations, the system may utilize a second camera and/or deep learning in order to determine a three-dimensional (3D) orientation of a target surgical tool. In various implementations, system 102 determines the position of the tip of the surgical tool and determines the orientation of the surgical tool in real-time.

The system achieves high accuracy by eliminating incorrect key point prediction using topological relationship among key points and key point validation. For example, in various implementations, the system carries out a validation process that is carried out to eliminate incorrect key points prediction. The system may perform such a validation process based on topological relationships among key points. For example, the system may determine the distance between two or more key points. If a given key point is substantially distant from a cluster or line of other key points, the system may deem the given key point as an outlier and may ignore the given key point. The system may apply these and similar techniques to different portions of a target surgical tool (e.g., tool tip or tips, tool components such as the tool shaft, etc.).

In some implementations, the system may determine a key point confidence score for each key point of the surgical tool. In various implementations, each key point confidence score indicates an accuracy level of the determination of a corresponding key point. Confidence scores may range from low to high (e.g., 0.0 to 1.0, 0%, to 100%, etc.). In some implementations, key points associated with confidence scores that fall below a predetermined confidence threshold may be deemed as outliers to be ignored. The predetermined confidence threshold may vary, depending on the particular implementation. In some implementations, the system may rank confidence scores of key points and eliminate key points associated with confidence scores that fall below a predetermined rank threshold. The predetermined rank threshold may vary, depending on the particular implementation.

In various implementations, the system uses deep learning for tool detection and key points estimation on the surgical tool. From information associated with tool detection and key points estimation on the surgical tool, the system further determines the position of the tip of the surgical tool and determines the orientation of the surgical tool. In some implementations, the may determine the position of the tip of the surgical tool and the orientation of the surgical too based at least in part on deep learning. In various implementations, the system may process thousands of image frames in order to build a training dataset to detect and identify features of a target surgical tool in real time. This achieves an optimal result by integrating topological information for key point prediction validation.

In various implementations, the system utilizes a deep learning network to detect and classify objects including a target surgical tool in an image frame. The system may employ deep learning techniques to classify tools, which provides a lightweight model for accuracy and speed. The system may also use deep learning to distinguish between a primary or dominant surgical tool such as scissors and a secondary or assistive surgical tool such as a grasper. For example, the surgeon may use a grasper to grab particular tissue to pull away from tissue to be cut by scissors or a clipper.

In various implementations, the system utilizes a deep learning network to classify the objects into the various tool classifications. In some implementations, the system uses a classifier that is trained with known features learned by the deep learning network. The system uses the known features to determine the type of tool or tool classification based on the features that the system recognizes in the image frame.

While various implementations are described in the context of the example surgical tool being scissors or a clipper, these implementations and others also apply to various other types of tools. For example, tools may include cutting or dissecting instruments such as scalpels, scissors, saws, etc. Tools may include bipolar forceps and irrigators. Tools may include grasping or holding instruments such as smooth and toothed forceps, towel clamps, vascular clamps, organ holders, etc. Tools may include hemostatic instruments such as clamps, hemostatic forceps, atraumatic hemostatic forceps, etc. Tools may include retractor instruments such as C-shaped laminar hooks, blunt-toothed hooks, sharp-toothed hooks, grooved probes, tamp forceps, etc. Tools may include tissue unifying instruments and materials such as needle holders, surgical needles, staplers, clips, adhesive tapes, etc. The particular tools detected may vary, and will depend on the particular implementation. While implementations are described herein in the context of surgical tools, these implementations and others may also apply to other tools (e.g., non-surgical tools).

Detecting and identifying the dominant tool (e.g., dominant surgical tool) in real-time is beneficial for various natural user interfaces. For example, given the position of dominant tool, a camera can automatically move towards the tool such that the tool is re-centered. This provides a better view for the user (e.g., surgeon, etc.). In various implementations, in order to locate the dominant tool in every frame of a video, different types of models may be trained. As such, all the predictions may be combined in a systematical way to produce the final results.

Implementations described herein provide various benefits. For example, implementations determine the position or location of one or more surgical tool tips during surgery. Implementations also determine the orientation of a surgical tool, including the orientation of various components of a surgical tool during surgery.

Implementations described herein may be used in various applications in computer-based assistances for different kinds of surgeries. For example implementations may be applied to procedures involving endoscopy and laparoscopy. Implementations may be used to automatically adjust a camera during surgery (e.g., to place the surgical tool tip in the center of the image, for autofocusing, etc.). Implementations may be used with robotic arms during surgery (e.g., camera holder, tool holder, etc.). Implementation may also be used to provide warnings (e.g., if a surgical tool tip is too close to a particular part of an organ, etc.).

Figure 7:
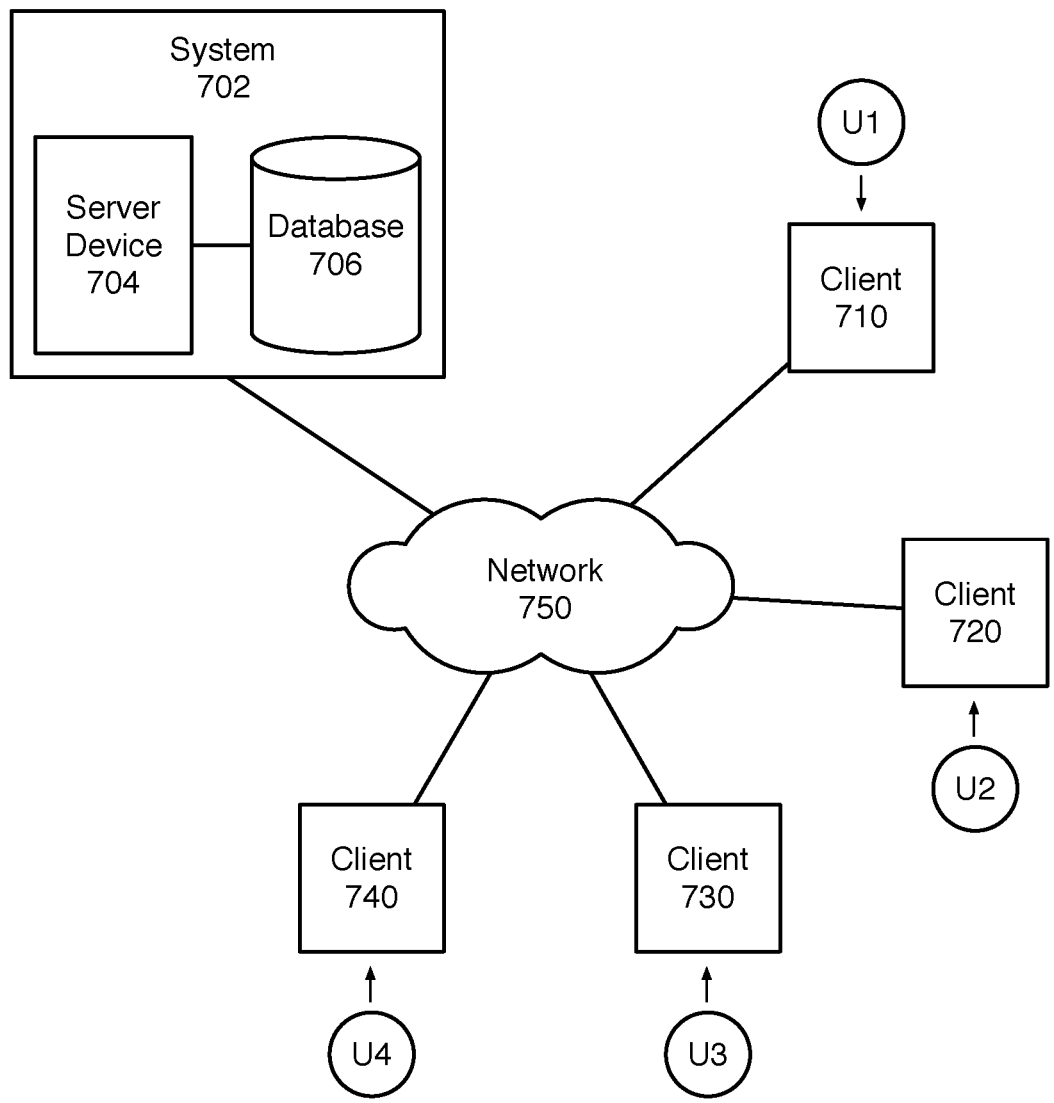
FIG. 7 illustrates a block diagram of an example network environment, which may be used for some implementations described herein.

FIG. 7 illustrates a block diagram of an example network environment 700, which may be used for some implementations described herein. In some implementations, network environment 700 includes a system 702, which includes a server device 704 and a network database 706. Network environment 700 also includes client devices 710, 720, 730, and 740, which may communicate with each other directly or via system 702. Client devices 710, 720, 730, and 740 may include viewer clients, cameras, and other surgical related devices. Network environment 700 also includes a network 750.

For ease of illustration, FIG. 7 shows one block for each of system 702, server device 704, and network database 706, and shows four blocks for client devices 710, 720, 730, and 740. While some implementations are described in the context of one client device being used to view a video of a surgery procedure (e.g., one surgeon viewing the video), these implementations and others may apply to multiple client devices. For example, there may be other physicians, and/or other clinicians, and/or students viewing the video.

Blocks 702, 704, and 706 may represent multiple systems, server devices, and network databases. Also, there may be any number of client devices. In other implementations, network environment 700 may not have all of the components shown and/or may have other elements including other types of elements instead of, or in addition to, those shown herein. In various implementations, users U1, U2, U3, and U4 may interact with each other or with system 702 using respective client devices 710, 720, 730, and 740.

In the various implementations described herein, a processor of system 702 and/or a processor of any client device 710, 720, 730, and 740 causes the elements described herein (e.g., information, etc.) to be displayed in a user interface on one or more display screens.

Implementations may apply to any network system and/or may apply locally for an individual user. For example, implementations described herein may be implemented by system 702 and/or any client device 710, 720, 730, and 740. System 702 may perform the implementations described herein on a stand-alone computer, tablet computer, smartphone, etc. System 702 and/or any of client devices 710, 720, 730, and 740 may perform implementations described herein individually or in combination with other devices.

Figure 8:
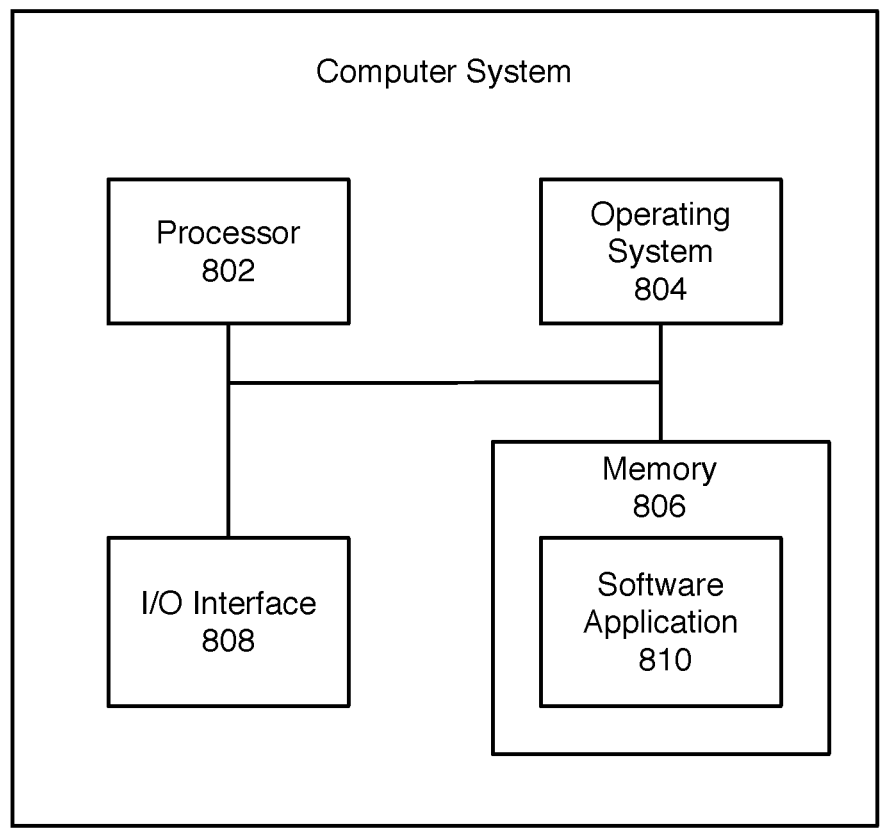
FIG. 8 illustrates a block diagram of an example computing system, which may be used for some implementations described herein.

FIG. 8 illustrates a block diagram of an example computer system 800, which may be used for some implementations described herein. For example, computer system 800 may be used to implement system 102 of FIG. 1 and/or system 702 of FIG. 7, as well as to perform implementations described herein. In some implementations, computer system 800 may include a processor 802, an operating system 804, a memory 806, and an input/output (I/O) interface 808. In various implementations, processor 802 may be used to implement various functions and features described herein, as well as to perform the method implementations described herein. While processor 802 is described as performing implementations described herein, any suitable component or combination of components of computer system 800 or any suitable processor or processors associated with computer system 800 or any suitable system may perform the steps described. Implementations described herein may be carried out on a user device, on a server, or a combination of both.

Computer system 800 also includes a software application 810, which may be stored on memory 806 or on any other suitable storage location or computer-readable medium. Software application 810 provides instructions that enable processor 802 to perform the implementations described herein and other functions. Software application may also include an engine such as a network engine for performing various functions associated with one or more networks and network communications. The components of computer system 800 may be implemented by one or more processors or any combination of hardware devices, as well as any combination of hardware, software, firmware, etc.

For ease of illustration, FIG. 8 shows one block for each of processor 802, operating system 804, memory 806, I/O interface 808, and software application 810. These blocks 802, 804, 806, 808, and 810 may represent multiple processors, operating systems, memories, I/O interfaces, and software applications. In various implementations, computer system 800 may not have all of the components shown and/or may have other elements including other types of components instead of, or in addition to, those shown herein.

Although the description has been described with respect to particular embodiments thereof, these particular embodiments are merely illustrative, and not restrictive. Concepts illustrated in the examples may be applied to other examples and implementations.

In various implementations, software is encoded in one or more non-transitory computer-readable media for execution by one or more processors. The software when executed by one or more processors is operable to perform the implementations described herein and other functions.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a non-transitory computer-readable storage medium (also referred to as a machine-readable storage medium) for use by or in connection with the instruction execution system, apparatus, or device. Particular embodiments can be implemented in the form of control logic in software or hardware or a combination of both. The control logic when executed by one or more processors is operable to perform the implementations described herein and other functions. For example, a tangible medium such as a hardware storage device can be used to store the control logic, which can include executable instructions.

Particular embodiments may be implemented by using a programmable general purpose digital computer, and/or by using application specific integrated circuits, programmable logic devices, field programmable gate arrays, optical, chemical, biological, quantum or nanoengineered systems, components and mechanisms. In general, the functions of particular embodiments can be achieved by any means as is known in the art. Distributed, networked systems, components, and/or circuits can be used. Communication, or transfer, of data may be wired, wireless, or by any other means.

A "processor" may include any suitable hardware and/or software system, mechanism, or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems. A computer may be any processor in communication with a memory. The memory may be any suitable data storage, memory and/or non-transitory computer-readable storage medium, including electronic storage devices such as random-access memory (RAM), read-only memory (ROM), magnetic storage device (hard disk drive or the like), flash, optical storage device (CD, DVD or the like), magnetic or optical disk, or other tangible media suitable for storing instructions (e.g., program or software instructions) for execution by the processor. For example, a tangible medium such as a hardware storage device can be used to store the control logic, which can include executable instructions. The instructions can also be contained in, and provided as, an electronic signal, for example in the form of software as a service (SaaS) delivered from a server (e.g., a distributed system and/or a cloud computing system).

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

What is claimed is:

1. A system comprising:
one or more processors; and
logic encoded in one or more non-transitory computer-readable storage media for execution by the one or more processors and when executed operable to perform operations comprising:
receiving at least one image frame of a plurality of image frames;
detecting a surgical tool in the at least one image frame;
determining one or more attributes of the surgical tool, wherein the one or more attributes comprise one or more components of the surgical tool, a configuration of the surgical tool, a configuration of the one or more components of the surgical tool, and a shape of the surgical tool;
generating a plurality of key points based on the one or more attributes of the surgical tool, wherein each key point of the key points corresponds to a different portion of the surgical tool, wherein at least one key point of the key points corresponds to a tip of the surgical tool, and wherein at least one key point of the key points corresponds to a shaft of the surgical tool;
determining a position of the tip and the shaft of the surgical tool based on the key points; and
determining an orientation of the tip and the shaft of the surgical tool based on the key points, wherein the orientation comprises a distal end of the shaft and a proximal end of the shaft.

2. The system of claim 1, wherein the logic when executed is further operable to perform operations comprising:
determining a plurality of orientations of a plurality of corresponding portions of the surgical tool;
determining lengths of one or more portions of the surgical tool; and
determining angles between two or more portions of the surgical tool.

3. The system of claim 1, wherein the logic when executed is further operable to perform operations comprising performing a validation process to eliminate incorrect key points, and wherein the validation process is based on topological relationships among key points.

4. The system of claim 3, wherein the logic when executed is further operable to perform operations comprising determining a key point confidence score for each key point of the plurality of key points of the surgical tool, wherein each key point confidence score indicates an accuracy level of each corresponding key point, and wherein key points having confidence scores that fall below a predetermined confidence threshold are deemed incorrect key points.

5. The system of claim 1, wherein the logic when executed is further operable to perform operations comprising determining the orientation of the surgical tool based on the plurality of key points.

6. The system of claim 1, wherein the logic when executed is further operable to perform operations comprising determining the position of the tip of the surgical tool and determining the orientation of the surgical tool in real-time.

7. The system of claim 1, wherein the logic when executed is further operable to perform operations comprising determining the position of the tip of the surgical tool and determining the orientation of the surgical tool based on deep learning.

8. A non-transitory computer-readable storage medium with program instructions stored thereon, the program instructions when executed by one or more processors are operable to perform operations comprising:
receiving at least one image frame of a plurality of image frames;
detecting a surgical tool in the at least one image frame;
determining one or more attributes of the surgical tool, wherein the one or more attributes comprise one or more components of the surgical tool, a configuration of the surgical tool, a configuration of the one or more components of the surgical tool, and a shape of the surgical tool;
generating a plurality of key points based on the one or more attributes of the surgical tool, wherein each key point of the key points corresponds to a different portion of the surgical tool, wherein at least one key point of the key points corresponds to a tip of the surgical tool, and wherein at least one key point of the key points corresponds to a shaft of the surgical tool;
determining a position of the tip and the shaft of the surgical tool based on the key points; and
determining an orientation of the tip and the shaft of the surgical tool based on the key points, wherein the orientation comprises a distal end of the shaft and a proximal end of the shaft.

9. The computer-readable storage medium of claim 8, wherein each key point of the plurality of key points corresponds to a different portion of the surgical tool.

10. The computer-readable storage medium of claim 8, wherein the instructions when executed are further operable to perform operations comprising determining the position of the tip of the surgical tool based on at least one key point of the plurality of key points that corresponds to the tip of the surgical tool.

11. The computer-readable storage medium of claim 8, wherein the instructions when executed are further operable to perform operations comprising determining the orientation of the surgical tool based on the plurality of key points.

12. The computer-readable storage medium of claim 8, wherein the instructions when executed are further operable to perform operations comprising determining the position of the tip of the surgical tool and determining the orientation of the surgical tool in real-time.

13. The computer-readable storage medium of claim 8, wherein the instructions when executed are further operable to perform operations comprising determining a key point confidence score for each key point of the plurality of key points of the surgical tool.

14. The computer-readable storage medium of claim 8, wherein the instructions when executed are further operable to perform operations comprising determining the position of the tip of the surgical tool and determining the orientation of the surgical tool based on deep learning.

15. A computer-implemented method comprising:
receiving at least one image frame of a plurality of image frames;
detecting a surgical tool in the at least one image frame;
determining one or more attributes of the surgical tool, wherein the one or more attributes comprise one or more components of the surgical tool, a configuration of the surgical tool, a configuration of the one or more components of the surgical tool, and a shape of the surgical tool;
generating a plurality of key points based on the one or more attributes of the surgical tool, wherein each key point of the key points corresponds to a different portion of the surgical tool, wherein at least one key point of the key points corresponds to a tip of the surgical tool, wherein at least one key point of the key points corresponds to a shaft of the surgical tool;
determining a position of the tip and the shaft of the surgical tool based on the key points; and
determining an orientation of the tip and the shaft of the surgical tool based on the key points, wherein the orientation comprises a distal end of the shaft and a proximal end of the shaft.

16. The method of claim 15, wherein each key point of the plurality of key points corresponds to a different portion of the surgical tool.

17. The method of claim 15, further comprising determining the position of the tip of the surgical tool based on at least one key point of the plurality of key points that corresponds to the tip of the surgical tool.

18. The method of claim 15, further comprising determining the orientation of the surgical tool based on the plurality of key points.

19. The method of claim 15, further comprising determining the position of the tip of the surgical tool and determining the orientation of the surgical tool in real-time.

20. The method of claim 15, further comprising determining a key point confidence score for each key point of the plurality of key points of the surgical tool.

* * * * *